(12) United States Patent
Martin et al.

(10) Patent No.: US 11,497,895 B2
(45) Date of Patent: *Nov. 15, 2022

(54) EXPANDABLE TIP MEDICAL DEVICES AND METHODS

(71) Applicant: Covidien LP, Mansfield, MA (US)

(72) Inventors: Brian Martin, Felton, CA (US); Nestor Aganon, San Jose, CA (US); Edward McGarry, San Jose, CA (US)

(73) Assignee: COVIDIEN LP, Mansfield, MA (US)

( * ) Notice: Subject to any disclaimer, the term of this patent is extended or adjusted under 35 U.S.C. 154(b) by 618 days.

This patent is subject to a terminal disclaimer.

(21) Appl. No.: 16/561,526

(22) Filed: Sep. 5, 2019

(65) Prior Publication Data

US 2020/0030583 A1 Jan. 30, 2020

Related U.S. Application Data

(62) Division of application No. 15/040,119, filed on Feb. 10, 2016, now Pat. No. 10,456,560.

(60) Provisional application No. 62/115,006, filed on Feb. 11, 2015.

(51) Int. Cl.
*A01B 5/00* (2006.01)
*A61M 25/09* (2006.01)
*A61M 25/04* (2006.01)

(52) U.S. Cl.
CPC ............ *A61M 25/09* (2013.01); *A61M 25/04* (2013.01); *A61M 25/0905* (2013.01); *A61M 25/09041* (2013.01); *A61M 2025/091* (2013.01); *A61M 2025/09058* (2013.01); *A61M 2025/09125* (2013.01); *A61M 2025/09133* (2013.01); *A61M 2025/09141* (2013.01); *A61M 2025/09175* (2013.01)

(58) Field of Classification Search
CPC .................. A61M 25/09; A61M 25/04; A61M 25/09041; A61M 25/0905; A61M 2025/09058; A61M 2025/091; A61M 2025/09125; A61M 2025/09133; A61M 2025/09141; A61M 2025/09175
See application file for complete search history.

(56) References Cited

U.S. PATENT DOCUMENTS

| | | |
|---|---|---|
| 2,918,919 A | 12/1959 | Wallace |
| 2,943,626 A | 7/1960 | Enrico |
| 3,996,938 A | 12/1976 | Clark, III |
| 4,347,846 A | 9/1982 | Dormia |
| 4,611,594 A | 9/1986 | Grayhack et al. |
| 4,650,466 A | 3/1987 | Luther |
| 4,657,020 A | 4/1987 | Lifton |
| 4,699,147 A | 10/1987 | Chilson et al. |
| 4,790,812 A | 12/1988 | Hawkins, Jr. et al. |
| 4,807,626 A | 2/1989 | Mcgirr |
| 4,832,055 A | 5/1989 | Palestrant |

(Continued)

FOREIGN PATENT DOCUMENTS

| | | |
|---|---|---|
| CN | 1640505 A | 7/2005 |
| CN | 102036611 A | 4/2011 |

(Continued)

*Primary Examiner* — May A Abouelela
(74) *Attorney, Agent, or Firm* — Fortem IP LLP; Mary Fox

(57) ABSTRACT

Guidewires and methods of use of guidewires having improved atraumatic tips that can distribute force to lessen trauma as well as anchor the guidewire to facilitate improved catheter exchange.

20 Claims, 7 Drawing Sheets

(56) References Cited

U.S. PATENT DOCUMENTS

| | | |
|---|---|---|
| 4,873,978 A | 10/1989 | Ginsburg |
| 4,969,891 A | 11/1990 | Gewertz |
| 4,998,539 A | 3/1991 | Delsanti |
| 5,034,001 A | 7/1991 | Garrison et al. |
| 5,057,114 A | 10/1991 | Wittich et al. |
| 5,059,178 A | 10/1991 | Ya |
| 5,102,415 A | 4/1992 | Guenther et al. |
| 5,147,400 A | 9/1992 | Kaplan et al. |
| 5,152,777 A | 10/1992 | Goldberg et al. |
| 5,192,286 A | 3/1993 | Phan et al. |
| 5,300,086 A | 4/1994 | Gory et al. |
| 5,329,942 A | 7/1994 | Gunther et al. |
| 5,443,478 A | 8/1995 | Purdy |
| 5,449,372 A | 9/1995 | Schmaltz et al. |
| 5,458,375 A | 10/1995 | Anspach, Jr. et al. |
| 5,490,859 A | 2/1996 | Mische et al. |
| 5,496,330 A | 3/1996 | Bates et al. |
| 5,509,900 A | 4/1996 | Kirkman |
| 5,653,684 A | 8/1997 | Laptewicz et al. |
| 5,658,296 A | 8/1997 | Bates et al. |
| 5,709,704 A | 1/1998 | Nott et al. |
| 5,733,302 A | 3/1998 | Myler et al. |
| 5,741,325 A | 4/1998 | Chaikof et al. |
| 5,792,156 A | 8/1998 | Perouse |
| 5,827,324 A | 10/1998 | Cassell et al. |
| 5,846,251 A | 12/1998 | Hart |
| 5,895,398 A | 4/1999 | Wensel et al. |
| 5,941,869 A | 8/1999 | Patterson et al. |
| 5,947,995 A | 9/1999 | Samuels |
| 5,968,090 A | 10/1999 | Ratcliff et al. |
| 5,971,938 A | 10/1999 | Hart et al. |
| 5,972,019 A | 10/1999 | Engelson et al. |
| 5,984,957 A | 11/1999 | Laptewicz, Jr. et al. |
| 6,001,118 A | 12/1999 | Daniel et al. |
| 6,033,394 A | 3/2000 | Vidlund et al. |
| 6,042,598 A | 3/2000 | Tsugita et al. |
| 6,053,932 A | 4/2000 | Daniel et al. |
| 6,066,149 A | 5/2000 | Samson et al. |
| 6,066,158 A | 5/2000 | Engelson et al. |
| 6,096,053 A | 8/2000 | Bates |
| 6,099,534 A | 8/2000 | Bates et al. |
| 6,146,403 A | 11/2000 | St. Germain |
| 6,159,220 A | 12/2000 | Gobron et al. |
| 6,165,200 A | 12/2000 | Tsugita et al. |
| 6,168,570 B1 | 1/2001 | Ferrera |
| 6,168,579 B1 | 1/2001 | Tsugita |
| 6,168,603 B1 | 1/2001 | Leslie et al. |
| 6,174,318 B1 | 1/2001 | Bates et al. |
| 6,176,873 B1 | 1/2001 | Ouchi |
| 6,190,394 B1 | 2/2001 | Lind et al. |
| 6,217,609 B1 | 4/2001 | Haverkost |
| 6,221,006 B1 | 4/2001 | Dubrul et al. |
| 6,245,088 B1 | 6/2001 | Lowery |
| 6,245,089 B1 | 6/2001 | Daniel et al. |
| 6,248,113 B1 | 6/2001 | Fina |
| 6,264,664 B1 | 7/2001 | Avellanet |
| 6,290,710 B1 | 9/2001 | Cryer et al. |
| 6,302,895 B1 | 10/2001 | Gobron et al. |
| 6,309,399 B1 | 10/2001 | Barbut et al. |
| 6,348,056 B1 | 2/2002 | Bates et al. |
| 6,350,266 B1 | 2/2002 | White et al. |
| 6,364,895 B1 | 4/2002 | Greenhalgh |
| 6,371,971 B1 | 4/2002 | Tsugita et al. |
| 6,383,195 B1 | 5/2002 | Richard |
| 6,383,196 B1 | 5/2002 | Leslie et al. |
| 6,391,044 B1 | 5/2002 | Yadav et al. |
| 6,402,771 B1 | 6/2002 | Palmer et al. |
| 6,409,750 B1 | 6/2002 | Hyodoh et al. |
| 6,416,505 B1 | 7/2002 | Fleischman et al. |
| 6,425,909 B1 | 7/2002 | Dieck et al. |
| 6,436,112 B2 | 8/2002 | Wensel et al. |
| 6,443,972 B1 | 9/2002 | Bosma et al. |
| 6,458,139 B1 | 10/2002 | Palmer et al. |
| 6,475,169 B2 | 11/2002 | Ferrera |
| 6,485,497 B2 | 11/2002 | Wensel et al. |
| 6,494,884 B2 | 12/2002 | Gifford, III et al. |
| 6,506,204 B2 | 1/2003 | Mazzocchi |
| 6,514,273 B1 | 2/2003 | Voss et al. |
| 6,530,935 B2 | 3/2003 | Wensel et al. |
| 6,540,657 B2 | 4/2003 | Cross, III et al. |
| 6,540,768 B1 | 4/2003 | Diaz et al. |
| 6,551,342 B1 | 4/2003 | Shen et al. |
| 6,575,997 B1 | 6/2003 | Palmer et al. |
| 6,585,753 B2 | 7/2003 | Eder et al. |
| 6,592,605 B2 | 7/2003 | Lenker et al. |
| 6,592,607 B1 | 7/2003 | Palmer et al. |
| 6,602,271 B2 | 8/2003 | Adams et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,620,148 B1 | 9/2003 | Tsugita |
| 6,635,068 B1 | 10/2003 | Dubrul et al. |
| 6,636,758 B2 | 10/2003 | Sanchez et al. |
| 6,638,245 B2 | 10/2003 | Miller et al. |
| 6,638,293 B1 | 10/2003 | Makower et al. |
| 6,641,590 B1 | 11/2003 | Palmer et al. |
| 6,645,199 B1 | 11/2003 | Jenkins et al. |
| 6,652,505 B1 | 11/2003 | Tsugita |
| 6,652,548 B2 | 11/2003 | Evans et al. |
| 6,660,021 B1 | 12/2003 | Palmer et al. |
| 6,663,650 B2 | 12/2003 | Sepetka et al. |
| 6,673,042 B1 | 1/2004 | Samson et al. |
| 6,679,893 B1 | 1/2004 | Tran |
| 6,685,738 B2 | 2/2004 | Chouinard et al. |
| 6,692,508 B2 | 2/2004 | Wensel et al. |
| 6,692,509 B2 | 2/2004 | Wensel et al. |
| 6,695,858 B1 | 2/2004 | Dubrul et al. |
| 6,702,782 B2 | 3/2004 | Miller et al. |
| 6,730,104 B1 | 5/2004 | Sepetka et al. |
| 6,745,080 B2 | 6/2004 | Koblish |
| 6,746,468 B1 | 6/2004 | Sepetka et al. |
| 6,749,619 B2 | 6/2004 | Ouriel et al. |
| 6,755,813 B2 | 6/2004 | Ouriel et al. |
| 6,800,080 B1 | 10/2004 | Bates |
| 6,824,545 B2 | 11/2004 | Sepetka et al. |
| 6,855,155 B2 | 2/2005 | Denardo et al. |
| 6,872,211 B2 | 3/2005 | White et al. |
| 6,872,216 B2 | 3/2005 | Daniel et al. |
| 6,890,341 B2 | 5/2005 | Dieck et al. |
| 6,893,431 B2 | 5/2005 | Naimark et al. |
| 6,905,503 B2 | 6/2005 | Gifford, III et al. |
| 6,913,612 B2 | 7/2005 | Palmer et al. |
| 6,936,059 B2 | 8/2005 | Belef |
| 6,939,362 B2 | 9/2005 | Boyle et al. |
| 6,945,977 B2 | 9/2005 | Demarais et al. |
| 6,953,465 B2 | 10/2005 | Dieck et al. |
| 6,964,672 B2 | 11/2005 | Brady et al. |
| 7,004,955 B2 | 2/2006 | Shen et al. |
| 7,004,956 B2 | 2/2006 | Palmer et al. |
| 7,037,320 B2 | 5/2006 | Brady et al. |
| 7,041,126 B2 | 5/2006 | Shin et al. |
| 7,044,134 B2 * | 5/2006 | Khairkhahan ... A61B 17/12022 606/198 |
| 7,048,014 B2 | 5/2006 | Hyodoh et al. |
| 7,058,456 B2 | 6/2006 | Pierce |
| 7,097,653 B2 | 8/2006 | Freudenthal et al. |
| 7,101,380 B2 | 9/2006 | Khachin et al. |
| 7,169,165 B2 | 1/2007 | Belef et al. |
| 7,179,273 B1 | 2/2007 | Palmer et al. |
| 7,182,771 B1 | 2/2007 | Houser et al. |
| 7,235,061 B2 | 6/2007 | Tsugita |
| 7,240,516 B2 | 7/2007 | Pryor |
| 7,279,000 B2 | 10/2007 | Cartier et al. |
| 7,285,126 B2 | 10/2007 | Sepetka et al. |
| 7,286,866 B2 | 10/2007 | Okerlund et al. |
| 7,288,112 B2 | 10/2007 | Denardo et al. |
| 7,294,311 B2 | 11/2007 | Coville |
| 7,300,428 B2 | 11/2007 | Ingenito |
| 7,303,758 B2 | 12/2007 | Falotico et al. |
| 7,306,619 B1 | 12/2007 | Palmer |
| 7,314,477 B1 | 1/2008 | Ravenscroft et al. |
| 7,314,728 B2 | 1/2008 | Toombs |
| 7,316,692 B2 | 1/2008 | Huffmaster |
| 7,329,265 B2 | 2/2008 | Burbank et al. |

(56) References Cited

U.S. PATENT DOCUMENTS

| | | | |
|---|---|---|---|
| 7,332,330 B2 | 2/2008 | Humes et al. | |
| 7,341,569 B2 | 3/2008 | Soltani et al. | |
| 7,344,550 B2 | 3/2008 | Carrison et al. | |
| 7,367,982 B2 | 5/2008 | Nash et al. | |
| 7,399,308 B2 | 7/2008 | Borillo et al. | |
| 7,491,210 B2 | 2/2009 | Dubrul et al. | |
| 7,534,252 B2 | 5/2009 | Sepetka et al. | |
| 7,578,830 B2 | 8/2009 | Kusleika et al. | |
| 7,621,870 B2 | 11/2009 | Berrada et al. | |
| 7,771,452 B2 * | 8/2010 | Pal | A61F 2/013 606/191 |
| 7,837,702 B2 | 11/2010 | Bates | |
| 7,850,708 B2 * | 12/2010 | Pal | A61F 2/01 623/23.72 |
| 8,070,791 B2 | 12/2011 | Ferrera et al. | |
| 8,088,140 B2 | 1/2012 | Ferrera et al. | |
| 8,105,333 B2 | 1/2012 | Sepetka et al. | |
| 8,197,493 B2 | 6/2012 | Ferrera et al. | |
| 8,216,269 B2 * | 7/2012 | Magnuson | A61F 2/0108 606/200 |
| 8,512,352 B2 | 8/2013 | Martin | |
| 8,535,334 B2 | 9/2013 | Martin | |
| 8,545,526 B2 | 10/2013 | Martin et al. | |
| 8,603,014 B2 | 12/2013 | Alleman et al. | |
| 8,795,315 B2 * | 8/2014 | Hunt | A61F 2/01 604/105 |
| 8,837,800 B1 | 9/2014 | Bammer et al. | |
| 9,119,656 B2 | 9/2015 | Bose et al. | |
| 9,126,018 B1 | 9/2015 | Garrison | |
| 9,204,887 B2 * | 12/2015 | Cully | A61B 17/221 |
| 9,211,132 B2 | 12/2015 | Bowman | |
| 9,241,699 B1 | 1/2016 | Kume et al. | |
| 9,265,512 B2 | 2/2016 | Garrison et al. | |
| 9,271,747 B2 | 3/2016 | Martin | |
| 9,308,007 B2 | 4/2016 | Cully et al. | |
| 9,399,118 B2 | 7/2016 | Kume et al. | |
| 9,445,828 B2 | 9/2016 | Turjman et al. | |
| 9,445,829 B2 | 9/2016 | Brady et al. | |
| 9,492,637 B2 | 11/2016 | Garrison et al. | |
| 9,539,022 B2 | 1/2017 | Bowman | |
| 9,561,345 B2 | 2/2017 | Garrison et al. | |
| 9,579,119 B2 | 2/2017 | Cully et al. | |
| 9,585,741 B2 | 3/2017 | Ma | |
| 9,642,635 B2 | 5/2017 | Vale et al. | |
| 9,655,633 B2 | 5/2017 | Leynov et al. | |
| 9,737,318 B2 | 8/2017 | Monstadt et al. | |
| 9,770,251 B2 | 9/2017 | Bowman et al. | |
| 9,801,643 B2 | 10/2017 | Hansen et al. | |
| 9,833,252 B2 * | 12/2017 | Sepetka | A61B 17/221 |
| 9,861,783 B2 | 1/2018 | Garrison et al. | |
| 9,901,434 B2 * | 2/2018 | Hoffman | A61F 2/0108 |
| 9,993,257 B2 | 6/2018 | Losordo et al. | |
| 10,028,782 B2 | 7/2018 | Orion | |
| 10,029,008 B2 | 7/2018 | Creighton | |
| 10,039,906 B2 | 8/2018 | Kume et al. | |
| 2001/0041909 A1 | 11/2001 | Tsugita et al. | |
| 2001/0044632 A1 | 11/2001 | Daniel et al. | |
| 2001/0044634 A1 | 11/2001 | Don et al. | |
| 2001/0051810 A1 | 12/2001 | Dubrul et al. | |
| 2002/0002396 A1 | 1/2002 | Fulkerson | |
| 2002/0004667 A1 | 1/2002 | Adams et al. | |
| 2002/0026211 A1 | 2/2002 | Khosravi et al. | |
| 2002/0058904 A1 | 5/2002 | Boock et al. | |
| 2002/0062135 A1 | 5/2002 | Mazzocchi et al. | |
| 2002/0072764 A1 | 6/2002 | Sepetka et al. | |
| 2002/0082558 A1 | 6/2002 | Samson et al. | |
| 2002/0123765 A1 | 9/2002 | Sepetka et al. | |
| 2002/0138094 A1 * | 9/2002 | Borillo | A61F 2/013 606/200 |
| 2002/0143349 A1 | 10/2002 | Gifford et al. | |
| 2002/0151928 A1 | 10/2002 | Leslie et al. | |
| 2002/0169473 A1 | 11/2002 | Sepetka et al. | |
| 2002/0169474 A1 * | 11/2002 | Kusleika | A61F 2/013 606/200 |
| 2002/0188314 A1 | 12/2002 | Anderson et al. | |
| 2002/0193812 A1 | 12/2002 | Patel et al. | |
| 2002/0193813 A1 | 12/2002 | Helkowski et al. | |
| 2002/0193825 A1 | 12/2002 | Mcguckin et al. | |
| 2003/0004533 A1 | 1/2003 | Dieck et al. | |
| 2003/0004542 A1 | 1/2003 | Wensel et al. | |
| 2003/0004568 A1 | 1/2003 | Ken et al. | |
| 2003/0023265 A1 | 1/2003 | Forber | |
| 2003/0040771 A1 | 2/2003 | Hyodoh et al. | |
| 2003/0050663 A1 | 3/2003 | Khachin et al. | |
| 2003/0060782 A1 | 3/2003 | Bose et al. | |
| 2003/0093087 A1 | 5/2003 | Jones et al. | |
| 2003/0093111 A1 | 5/2003 | Ken et al. | |
| 2003/0097114 A1 | 5/2003 | Ouriel et al. | |
| 2003/0144687 A1 | 7/2003 | Brady et al. | |
| 2003/0153935 A1 | 8/2003 | Mialhe | |
| 2003/0176884 A1 | 9/2003 | Berrada et al. | |
| 2003/0195556 A1 | 10/2003 | Stack et al. | |
| 2004/0068288 A1 | 4/2004 | Palmer et al. | |
| 2004/0073243 A1 | 4/2004 | Sepetka et al. | |
| 2004/0079429 A1 | 4/2004 | Miller et al. | |
| 2004/0098024 A1 | 5/2004 | Dieck et al. | |
| 2004/0133232 A1 * | 7/2004 | Rosenbluth | A61B 17/22032 606/200 |
| 2004/0138692 A1 | 7/2004 | Phung et al. | |
| 2004/0153025 A1 | 8/2004 | Seifert et al. | |
| 2004/0153118 A1 | 8/2004 | Clubb et al. | |
| 2004/0161451 A1 | 8/2004 | Pierce et al. | |
| 2004/0172056 A1 * | 9/2004 | Guterman | A61B 17/12186 623/1.11 |
| 2004/0199201 A1 | 10/2004 | Kellett et al. | |
| 2004/0199243 A1 | 10/2004 | Yodfat | |
| 2004/0210116 A1 | 10/2004 | Nakao | |
| 2004/0267301 A1 | 12/2004 | Boylan et al. | |
| 2005/0004594 A1 | 1/2005 | Nool et al. | |
| 2005/0033348 A1 | 2/2005 | Sepetka et al. | |
| 2005/0038447 A1 | 2/2005 | Huffmaster | |
| 2005/0043680 A1 | 2/2005 | Segal et al. | |
| 2005/0043756 A1 | 2/2005 | Lavelle et al. | |
| 2005/0049619 A1 | 3/2005 | Sepetka et al. | |
| 2005/0055033 A1 | 3/2005 | Leslie et al. | |
| 2005/0055047 A1 | 3/2005 | Greenhalgh | |
| 2005/0059995 A1 | 3/2005 | Sepetka et al. | |
| 2005/0080356 A1 | 4/2005 | Dapolito et al. | |
| 2005/0085826 A1 | 4/2005 | Nair et al. | |
| 2005/0085847 A1 | 4/2005 | Galdonik et al. | |
| 2005/0085849 A1 | 4/2005 | Sepetka et al. | |
| 2005/0090857 A1 | 4/2005 | Kusleika et al. | |
| 2005/0090858 A1 | 4/2005 | Pavlovic | |
| 2005/0125024 A1 | 6/2005 | Sepetka et al. | |
| 2005/0131450 A1 | 6/2005 | Nicholson et al. | |
| 2005/0137680 A1 | 6/2005 | Ortiz et al. | |
| 2005/0171566 A1 | 8/2005 | Kanamaru | |
| 2005/0203571 A1 | 9/2005 | Mazzocchi et al. | |
| 2005/0209609 A1 | 9/2005 | Wallace | |
| 2005/0216030 A1 | 9/2005 | Sepetka et al. | |
| 2005/0216050 A1 | 9/2005 | Sepetka et al. | |
| 2005/0222580 A1 | 10/2005 | Gifford et al. | |
| 2005/0228417 A1 | 10/2005 | Teitelbaum et al. | |
| 2005/0234501 A1 | 10/2005 | Barone | |
| 2005/0234505 A1 | 10/2005 | Diaz et al. | |
| 2005/0277978 A1 | 12/2005 | Greenhalgh | |
| 2005/0283166 A1 | 12/2005 | Greenhalgh | |
| 2005/0283182 A1 | 12/2005 | Pierce et al. | |
| 2005/0283186 A1 | 12/2005 | Berrada et al. | |
| 2005/0288686 A1 | 12/2005 | Sepetka et al. | |
| 2006/0004404 A1 | 1/2006 | Khachin et al. | |
| 2006/0009784 A1 | 1/2006 | Behl et al. | |
| 2006/0036280 A1 | 2/2006 | French et al. | |
| 2006/0047286 A1 | 3/2006 | West | |
| 2006/0058836 A1 | 3/2006 | Bose et al. | |
| 2006/0058837 A1 | 3/2006 | Bose et al. | |
| 2006/0058838 A1 | 3/2006 | Bose et al. | |
| 2006/0095070 A1 | 5/2006 | Gilson et al. | |
| 2006/0129166 A1 | 6/2006 | Lavelle | |
| 2006/0129180 A1 | 6/2006 | Tsugita et al. | |
| 2006/0155305 A1 | 7/2006 | Freudenthal et al. | |
| 2006/0190070 A1 | 8/2006 | Dieck et al. | |
| 2006/0195137 A1 | 8/2006 | Sepetka et al. | |

(56) References Cited

U.S. PATENT DOCUMENTS

| | | |
|---|---|---|
| 2006/0229638 A1 | 10/2006 | Abrams et al. |
| 2006/0253145 A1 | 11/2006 | Lucas |
| 2006/0259063 A1 | 11/2006 | Bates et al. |
| 2006/0276805 A1 | 12/2006 | Yu |
| 2006/0282111 A1 | 12/2006 | Morsi |
| 2006/0287668 A1 | 12/2006 | Fawzi et al. |
| 2007/0112374 A1 | 5/2007 | Paul et al. |
| 2007/0118165 A1 | 5/2007 | Demello et al. |
| 2007/0149996 A1 | 6/2007 | Coughlin |
| 2007/0185500 A1 | 8/2007 | Martin et al. |
| 2007/0185501 A1 | 8/2007 | Martin et al. |
| 2007/0197103 A1 | 8/2007 | Martin et al. |
| 2007/0198029 A1 | 8/2007 | Martin et al. |
| 2007/0198030 A1 | 8/2007 | Martin et al. |
| 2007/0198051 A1 | 8/2007 | Clubb et al. |
| 2007/0208367 A1 | 9/2007 | Fiorella et al. |
| 2007/0208371 A1 | 9/2007 | French et al. |
| 2007/0225749 A1 | 9/2007 | Martin et al. |
| 2007/0233236 A1 | 10/2007 | Pryor |
| 2007/0258971 A1 | 11/2007 | Heslet et al. |
| 2007/0265656 A1 | 11/2007 | Amplatz et al. |
| 2007/0270905 A1 | 11/2007 | Osborne |
| 2008/0015541 A1 | 1/2008 | Rosenbluth et al. |
| 2008/0050389 A1 | 2/2008 | Muzykantov et al. |
| 2008/0051708 A1 | 2/2008 | Kumar et al. |
| 2008/0058256 A1 | 3/2008 | Boone et al. |
| 2008/0065012 A1 | 3/2008 | Hebert et al. |
| 2008/0076722 A1 | 3/2008 | Roberts et al. |
| 2008/0077175 A1 | 3/2008 | Palmer |
| 2008/0091174 A1 | 4/2008 | Alam et al. |
| 2008/0095760 A1 | 4/2008 | Toombs |
| 2008/0109031 A1 | 5/2008 | Sepetka et al. |
| 2008/0114393 A1 | 5/2008 | Carrison et al. |
| 2008/0119888 A1 | 5/2008 | Huffmaster |
| 2008/0167678 A1 | 7/2008 | Morsi |
| 2008/0183198 A1 | 7/2008 | Sepetka et al. |
| 2008/0183206 A1 | 7/2008 | Batiste |
| 2008/0188885 A1 | 8/2008 | Sepetka et al. |
| 2008/0194993 A1 | 8/2008 | McLaren et al. |
| 2008/0206134 A1 | 8/2008 | Lo et al. |
| 2008/0249409 A1 | 10/2008 | Fraser et al. |
| 2008/0262487 A1 | 10/2008 | Wensel et al. |
| 2008/0262528 A1 | 10/2008 | Martin |
| 2008/0262532 A1 | 10/2008 | Martin |
| 2008/0264216 A1 | 10/2008 | Duffy |
| 2008/0269871 A1 | 10/2008 | Eli |
| 2008/0275464 A1 | 11/2008 | Abrams et al. |
| 2009/0069828 A1 | 3/2009 | Martin et al. |
| 2009/0105722 A1 | 4/2009 | Fulkerson et al. |
| 2009/0105737 A1 | 4/2009 | Fulkerson et al. |
| 2009/0125053 A1 | 5/2009 | Ferrera et al. |
| 2009/0171293 A1 | 7/2009 | Yang et al. |
| 2009/0192518 A1 | 7/2009 | Leanna et al. |
| 2009/0287291 A1 | 11/2009 | Becking et al. |
| 2009/0299393 A1 | 12/2009 | Martin et al. |
| 2010/0076452 A1 | 3/2010 | Sepetka et al. |
| 2010/0100106 A1 | 4/2010 | Ferrera |
| 2010/0174309 A1 | 7/2010 | Fulkerson et al. |
| 2010/0185210 A1 | 7/2010 | Hauser et al. |
| 2010/0217187 A1 | 8/2010 | Ferrera et al. |
| 2010/0256600 A1 | 10/2010 | Ferrera |
| 2010/0318097 A1 | 12/2010 | Cragg et al. |
| 2011/0160742 A1 | 6/2011 | Ferrera et al. |
| 2011/0160757 A1 | 6/2011 | Ferrera et al. |
| 2011/0160760 A1 | 6/2011 | Ferrera et al. |
| 2011/0160761 A1 | 6/2011 | Ferrera et al. |
| 2011/0160763 A1 | 6/2011 | Ferrera et al. |
| 2011/0166586 A1 | 7/2011 | Sepetka et al. |
| 2011/0224707 A1 | 9/2011 | Miloslavski et al. |
| 2011/0288572 A1 | 11/2011 | Martin |
| 2011/0319917 A1 | 12/2011 | Ferrera et al. |
| 2012/0143230 A1 | 6/2012 | Sepetka et al. |
| 2012/0197285 A1 | 8/2012 | Martin et al. |
| 2013/0030461 A1 | 1/2013 | Marks et al. |
| 2013/0281788 A1 | 10/2013 | Garrison |
| 2014/0031856 A1 | 1/2014 | Martin |
| 2014/0066895 A1 | 3/2014 | Kipperman |
| 2014/0207179 A1* | 7/2014 | Farhangnia ............ A61M 25/04 606/200 |
| 2014/0276074 A1 | 9/2014 | Warner |
| 2014/0343595 A1 | 11/2014 | Monstadt et al. |
| 2014/0358178 A1* | 12/2014 | Hewitt ............ A61B 17/12013 606/200 |
| 2015/0297250 A1 | 10/2015 | Farhat et al. |
| 2015/0351775 A1* | 12/2015 | Fulton, III ........ A61B 17/12109 606/191 |
| 2015/0359547 A1 | 12/2015 | Vale et al. |
| 2016/0015402 A1 | 1/2016 | Brady et al. |
| 2016/0015935 A1 | 1/2016 | Chan et al. |
| 2016/0038721 A1* | 2/2016 | Lorenzo ................ A61M 25/09 600/585 |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0151618 A1 | 6/2016 | Powers et al. |
| 2016/0157985 A1 | 6/2016 | Vo et al. |
| 2016/0199620 A1 | 7/2016 | Pokomey et al. |
| 2016/0296690 A1 | 10/2016 | Kume et al. |
| 2016/0302808 A1 | 10/2016 | Loganathan et al. |
| 2016/0375180 A1 | 12/2016 | Anzai |
| 2017/0079766 A1 | 3/2017 | Wang et al. |
| 2017/0079767 A1 | 3/2017 | Leon-yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0164963 A1 | 6/2017 | Goyal |
| 2017/0215902 A1 | 8/2017 | Leynov et al. |
| 2017/0224953 A1 | 8/2017 | Tran et al. |
| 2017/0281909 A1 | 10/2017 | Northrop et al. |
| 2017/0290599 A1 | 10/2017 | Youn et al. |
| 2018/0049762 A1 | 2/2018 | Seip et al. |
| 2018/0084982 A1 | 3/2018 | Yamashita et al. |
| 2018/0116717 A1 | 5/2018 | Taff et al. |
| 2018/0132876 A1 | 5/2018 | Zaidat |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0185614 A1 | 7/2018 | Garrison et al. |

FOREIGN PATENT DOCUMENTS

| | | |
|---|---|---|
| DE | 3501707 A1 | 7/1986 |
| DE | 102004040868 A1 | 3/2006 |
| DE | 102005059670 A1 | 6/2007 |
| EP | 0200668 A2 | 11/1986 |
| EP | 1312314 A1 | 5/2003 |
| EP | 2260898 A1 | 12/2010 |
| EP | 2319575 B1 | 11/2013 |
| JP | 2002537943 A | 11/2002 |
| JP | 2007522881 A | 8/2007 |
| JP | 2007252951 A | 10/2007 |
| JP | 2008539958 A | 11/2008 |
| JP | 2014004219 A | 1/2014 |
| JP | 6249841 B2 | 12/2017 |
| JP | 2018118132 A | 8/2018 |
| KR | 20180102877 A | 9/2018 |
| WO | WO 9409845 A1 | 5/1994 |
| WO | WO 9509586 A1 | 4/1995 |
| WO | WO 9601591 A1 | 1/1996 |
| WO | WO 9617634 A2 | 6/1996 |
| WO | WO 9619941 A1 | 7/1996 |
| WO | WO 9727808 A1 | 8/1997 |
| WO | WO 9727893 A1 | 8/1997 |
| WO | WO 9803120 A1 | 1/1998 |
| WO | WO 9916364 A1 | 4/1999 |
| WO | WO 0053120 A1 | 9/2000 |
| WO | WO 0072909 A1 | 12/2000 |
| WO | WO 0132254 A1 | 5/2001 |
| WO | WO 0154622 A1 | 8/2001 |
| WO | WO 0167967 A1 | 9/2001 |
| WO | WO 0180748 A2 | 11/2001 |
| WO | WO 0202162 A2 | 1/2002 |

(56) References Cited

FOREIGN PATENT DOCUMENTS

| | | |
|---|---|---|
| WO | WO 0228291 A2 | 4/2002 |
| WO | WO 03000334 A1 | 1/2003 |
| WO | WO 03061730 A2 | 7/2003 |
| WO | WO 03089039 A1 | 10/2003 |
| WO | WO 2006031410 A2 | 3/2006 |
| WO | WO 2006084019 A2 | 8/2006 |
| WO | WO 2006122076 A1 | 11/2006 |
| WO | WO 2007092820 A2 | 8/2007 |
| WO | 2007136660 A2 | 11/2007 |
| WO | WO 2007143602 A2 | 12/2007 |
| WO | WO 2008034615 A2 | 3/2008 |
| WO | WO 2008036156 A1 | 3/2008 |
| WO | WO 2008063156 A2 | 5/2008 |
| WO | WO 2008072243 A2 | 6/2008 |
| WO | WO 2008086180 A1 | 7/2008 |
| WO | WO 2008097956 A1 | 8/2008 |
| WO | WO 2008097998 A1 | 8/2008 |
| WO | WO 2008113122 A1 | 9/2008 |
| WO | WO 2008127287 A2 | 10/2008 |
| WO | WO 2008131116 A1 | 10/2008 |
| WO | WO 2009034456 A2 | 3/2009 |
| WO | WO 2009086482 A1 | 7/2009 |
| WO | WO 2011091383 A1 | 7/2011 |
| WO | WO 2012009675 A2 | 1/2012 |
| WO | WO 2012162437 A1 | 11/2012 |
| WO | WO 2013106146 A1 | 7/2013 |
| WO | WO 2014036113 A1 | 3/2014 |
| WO | WO 2015141317 A1 | 9/2015 |
| WO | WO 2017192999 A1 | 11/2017 |
| WO | WO 2018019829 A1 | 2/2018 |
| WO | WO 2018033401 A1 | 2/2018 |
| WO | WO 2018046408 A2 | 3/2018 |
| WO | WO 2018137029 A1 | 8/2018 |
| WO | WO 2018137030 A1 | 8/2018 |
| WO | WO 2018145212 A1 | 8/2018 |
| WO | WO 2018156813 A1 | 8/2018 |
| WO | WO 2018172891 A1 | 9/2018 |
| WO | WO 2018187776 A1 | 10/2018 |

\* cited by examiner

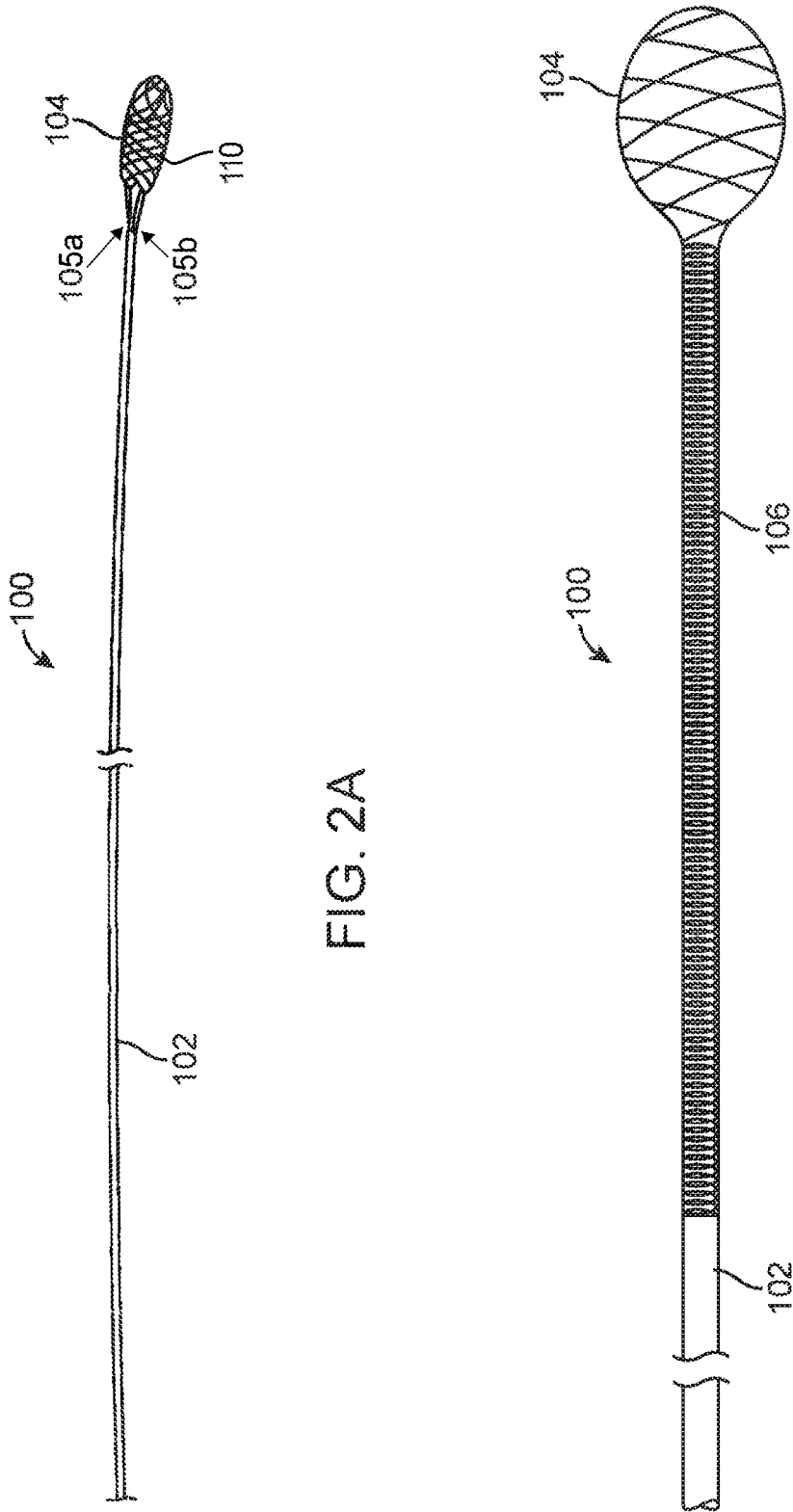

EXPANDABLE TIP MEDICAL DEVICES AND METHODS

CROSS-REFERENCE TO RELATED APPLICATION(S)

The present application is a divisional of U.S. patent application Ser. No. 15/040,119, filed Feb. 10, 2016, which claims the benefit of priority to U.S. Provisional Application No. 62/115,006, filed Feb. 11, 2015, the contents of each of which are incorporated by reference herein in their entireties.

FIELD

The disclosure provided herein relates to guidewires and other medical devices having improved atraumatic tips that can distribute force to lessen trauma as well as anchor the guidewire or device to facilitate improved catheter insertion, removal and/or exchange.

BACKGROUND

Exchange length guidewires are often used during procedures in interventional radiology, including interventional cardiology, interventional neuroradiology, and interventional peripheral radiology.

The exchange length guidewires are used to facilitate exchanging of devices such as catheters or microcatheters, over a guidewire where, e.g., the physician removes a first microcatheter from a guidewire that is positioned at a site of interest and then advances a second microcatheter over the guidewire to that site in the vasculature.

For example, a physician may replace the original microcatheter with another catheter or a separate device having different properties or better suited for the intended procedure (e.g. better condition, more navigable, better supporting, etc.). For example, a first microcatheter can be used with properties that allow for accessing or navigation to the target site but a second microcatheter might be better suited to support or provide access for medical devices to the target site. Regardless, a physician performs a procedure for catheter exchange by placing a first microcatheter at a desired location within the vasculature often using a standard guidewire. Next, the physician removes the standard guidewire from the first microcatheter while leaving the first microcatheter at the site. The physician then inserts an exchange length guidewire (usually 280 cm to 300 cm in length) through the first microcatheter and positions a distal end of the exchange length guidewire at the intended site.

Once this exchange length guidewire is loaded into the microcatheter and positioned in the anatomy, the first microcatheter can be removed and replaced with a different microcatheter. The extra length of the exchange length guidewire enables the removal and replacement of the microcatheter (referred to as an exchange procedure) without loss of direct access to the proximal end of the guidewire by the physician.

The physician must perform an exchange procedure with caution because excessive movement of the tip of the exchange guidewire can cause irritation or even damage to the vessel. This is especially true for delicate vasculature such as the neurovasculature. In some extreme cases, excessive movement of the guidewire tip can perforate the vessel wall during the exchange procedure. Because of this, the exchange procedure typically takes place very slowly, where the physician removes the first microcatheter in incremental movements by holding the proximal end of the exchange guidewire and while simultaneously trying to prevent excessive movement of the exchange guidewire. Once the physician removes the first microcatheter, the physician advances a second microcatheter over the exchange guidewire and navigates the second microcatheter distally again while holding the proximal end of the guidewire and preventing as much motion as possible.

However, even with near immobilization of the proximal end of the guidewire, the distal end of the guidewire may still move more than desired. This unwanted motion can be the result of imprecise holding of the guidewire, or the result of the advancement of the microcatheter which causes undesired motion of the guidewire, or the result of patient movement during the breathing cycle, etc.

In any case, it is this unintended motion of the distal end of the guidewire that can cause the vessel irritation, spasm, dissection, and/or perforation. Physicians often curve the distal end of the guidewire to attempt to make it less traumatic; this practice may help somewhat but it may not lower the risk of vessel damage sufficiently. For example, as shown in FIG. 1, a microcatheter 12 advances along a guidewire 14 having a "J-tip" or "J-curve" 16. However, the J-curve 16 does not distribute the force sufficiently and can cause trauma to the walls of the vessel 10 along the portion of the guidewire 14 that is shaped into the curve 16.

SUMMARY

The illustrations and variations described herein are meant to provide examples of the methods and devices of the subject technology. It is contemplated that combinations of aspects of specific embodiments or combinations of the specific embodiments themselves are within the scope of this disclosure.

The examples discussed herein show the devices and methods of the present disclosure in a form that is suitable to assist in catheter exchange procedures. However, the guidewires described herein can be used for any vascular or non-vascular access procedure in which a guidewire is used to assist in accessing a target site within the anatomy.

It should also be noted that although this disclosure discusses exchange length guidewires, the improved guidewires of this disclosure can be manufactured in any length, e.g., a shorter length for a standard guide wire length. In this case, the physician can remove the original procedural guidewire and replace it with the expandable tipped guidewire disclosed herein. This could be desired if the physician does not plan to replace or exchange a microcatheter but nonetheless prefers a wire that is more atraumatic and/or offers anchoring for enhanced navigation or manipulation of the catheter.

In one example, an improved guidewire comprises a guidewire body having a distal end; a plurality of elements extending along a distal portion of the guidewire body and diverging from the distal end of the guidewire body to form a compliant structure having an expanded profile that is greater than a radial dimension of the distal end of the guidewire body and being resiliently deformable to a reduced profile, where in the expanded profile the compliant structure optionally provides a uniform radial force in an outward circumferential direction from an axis of the guidewire body; and where the plurality of elements return to the distal portion of the guidewire body and extend along a distal portion of the guide wire body.

Variations of the guidewires can include a guidewire body comprising a solid core member and where the plurality of elements are affixed to the solid core member along the portion of the proximal end of the guide wire body.

The compliant structure, and/or the anchoring portions of the devices can optionally be made to be fluid permeable to allow fluid flow therethrough.

Variations of the devices include compliant structures where the plurality of strut member comprise at least a first strut and a second strut, where a cross sectional area of the first strut is different than a cross sectional area of the second strut. The struts and/or elements forming the compliant structure can be interwoven or braided to form the compliant structure. In some variations, the struts/element can be interwoven and braided in various parts of the compliant structure.

In some variations of the device, the plurality of elements on the distal portion of the guidewire body increase a column strength of the distal portion of the guidewire body.

In another variation, the improved guidewire comprises a guidewire body extending between a proximal portion and a distal portion, the guidewire body comprising an elongated shape and configured to navigate the tortuous anatomy; a plurality of strut members arranged to form a frame member having a diameter greater than a cross sectional diameter of the distal portion of the guidewire body; where the plurality of elements in the frame member can move relative to each other causing the frame member to be compliant and optionally provide a uniform radial force in an outward circumferential direction from the guidewire body when released from a constraining force; and the plurality of elements converging from a proximal end of the frame member to extend along the distal portion of the guidewire body, where the plurality of elements are continuous.

The present disclosure also includes improved methods of performing a catheter exchange procedure. One example includes inserting a catheter into a blood vessel having a flow of blood therethrough and positioning a first catheter into the blood vessel; advancing a guidewire into the first catheter, where the guidewire comprises a guidewire body extending between a proximal end and a distal end, and a compliant structure located at the distal end of the guidewire body, where a first portion of the compliant structure is collapsible to permit advancement through the first catheter and self-expandable upon deployment from the first catheter, where a proximal portion of the compliant structure is continuous and extends along a proximal portion of the guidewire; deploying the compliant structure into the blood vessel from a distal end of the first catheter such that the compliant structure optionally expands in a uniform radial direction from the guidewire body against the blood vessel thereby permitting a distribution of force against the blood vessel allowing for the compliant structure to temporarily anchor the guidewire within the blood vessel; withdrawing the first catheter out of the blood vessel while maintaining the guidewire within the blood vessel; and advancing a second catheter over the guidewire.

In another variation, the guidewire devices described herein are fabricated in a manner that eliminates or reduces the number of joints and/or connection points in the device. Doing so allows the device to have a compact and smooth configuration making it easier for delivery through a microcatheter; and leads to a safer device less prone to breaking.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A guidewire comprising:
a guidewire body having a distal end;
a plurality of elements having a proximal section extending along a distal portion of the guidewire body, and a distal section in which the plurality of elements diverge radially outward from the distal end of the guidewire body to form a compliant structure having an expanded profile that is greater than a radial dimension of the distal end of the guidewire body and being resiliently deformable to a reduced profile, where in the expanded profile the compliant structure provides a radial force in an outward circumferential direction from an axis of the guidewire body.

Clause 2. The guidewire of Clause 1, where the guidewire body comprises a core member and where the plurality of elements, in said proximal section, are affixed to the core member along the distal end of the guidewire body.

Clause 3. The guidewire of Clause 2, where the plurality of elements, in said proximal section, are not radially expandable away from the core member.

Clause 4. The guidewire of Clause 1, where the compliant structure comprises a shape selected from the group consisting of spherical, egg-shaped, football-shaped, elliptical, conical, cylindrical.

Clause 5. The guidewire of Clause 1, where the plurality of elements comprises at least a first strut and a second strut, where a cross sectional area of the first strut is different than a cross sectional area of the second strut.

Clause 6. The guidewire of Clause 1, where the plurality of elements forming the compliant structure are interwoven to form the compliant structure.

Clause 7. The guidewire of Clause 1, where the plurality of elements forming the compliant structure are braided to form the compliant structure.

Clause 8. The guidewire of Clause 1, where at least one of the plurality of elements forming the compliant structure is heat set.

Clause 9. The guidewire of Clause 1, where at least one of the plurality of elements forming the compliant structure comprises a material selected from the group consisting of a drawn filled tube, a nitinol wire, a shape memory alloy, a super-elastic alloy, a stainless steel material, and a platinum material.

Clause 10. The guidewire of Clause 1, where the plurality of elements, in said proximal section, are bonded to the guidewire body.

Clause 11. The guidewire of Clause 1, where the plurality of elements on the distal portion of the guidewire body increase a column strength of the distal portion of the guidewire body.

Clause 12. The guidewire of Clause 1, where the guidewire body comprises a core member and where the plurality of elements, in said proximal section, are affixed against the solid core member along the distal end of the guidewire body.

Clause 13. The guidewire of Clause 1, where the compliant structure is permeable to allow fluid flow therethrough.

Clause 14. A guidewire for advancing through a body lumen in a tortuous anatomy, the guidewire comprising:
a guidewire body extending between a proximal portion and a distal portion, the guidewire body comprising an elongated shape and configured to navigate the tortuous anatomy;

a plurality of elements arranged to form a frame member having a diameter greater than a cross sectional diameter of the distal portion of the guidewire body;

where the plurality of elements in the frame member can move relative to each other causing the frame member to be compliant and provide a radial force in an outward circumferential direction from the guidewire body when released from a constraining force; and the plurality of elements converging from a proximal region of the frame member to extend proximally from the frame member along the distal portion of the guidewire body, thereby forming a proximal extension of the plurality of elements, where the plurality of elements are continuous from the frame member into the proximal extension along the distal portion of the guidewire body.

Clause 15. The guidewire of Clause 14, where the guidewire body comprises a core member and where the plurality of elements are affixed to the core member along the proximal extension of the plurality of elements.

Clause 16. The guidewire of Clause 15, where the plurality of elements, in said proximal extension, are not radially expandable away from the core member.

Clause 17. The guidewire of Clause 14, where the frame member comprises a shape selected from the group consisting of spherical, egg-shaped, football-shaped, elliptical, conical, cylindrical.

Clause 18. The guidewire of Clause 14, where the plurality of elements comprises at least a first strut and a second strut, where a cross sectional area of the first strut is different than a cross sectional area of the second strut.

Clause 19. The guidewire of Clause 14, where the plurality of elements forming the frame member are interwoven to form the frame member.

Clause 20. The guidewire of Clause 14, where the plurality of elements forming the frame member are braided to form the frame member.

Clause 21. The guidewire of Clause 14, where the frame member is permeable to allow fluid flow therethrough.

Clause 22. The guidewire of Clause 14, where at least one of the plurality of elements forming the frame member comprises a material selected from the group consisting of a drawn filled tube, a nitinol wire, a shape memory alloy, a super-elastic alloy, a stainless steel material, and a platinum material.

Clause 23. The guidewire of Clause 14, where the plurality of elements, in said proximal extension, are bonded to the guidewire body.

Clause 24. The guidewire of Clause 14, where the plurality of elements in said proximal extension increase a column strength of a distal portion of the guidewire body.

Clause 25. The guidewire of Clause 1, where the guidewire body comprises a core member and where the plurality of elements, in said proximal section, are affixed against the solid core member along the distal end of the guidewire body.

Clause 26. A method of inserting a catheter into a blood vessel having a flow of blood therethrough, the method comprising:

positioning a first catheter into the blood vessel;

advancing a guidewire into the first catheter, where the guidewire comprises a guidewire body extending between a proximal end and a distal end, and a compliant structure located at the distal end of the guidewire body, where a first portion of the compliant structure is collapsible to permit advancement through the first catheter and self-expandable upon deployment from the first catheter, where a proximal portion of the compliant structure is continuous and extends along a distal portion of the guidewire;

deploying the compliant structure into the blood vessel from a distal end of the first catheter such that the compliant structure expands in a uniform radial direction from the guidewire body against the blood vessel thereby permitting a distribution of force against the blood vessel allowing for the compliant structure to temporarily anchor the guidewire within the blood vessel;

withdrawing the first catheter out of the blood vessel while maintaining the guidewire within the blood vessel; and advancing a second catheter over the guidewire.

BRIEF DESCRIPTION OF THE DRAWINGS

Each of the following figures diagrammatically illustrates aspects and variation to better understand the invention. Variation of the invention from the aspects shown in the figures is contemplated.

FIG. 2A illustrates an example of an improved guidewire having a guidewire body 102 and compliant member.

FIG. 2B illustrates a magnified view of a distal section of an improved guidewire.

DETAILED DESCRIPTION

Figure 1:
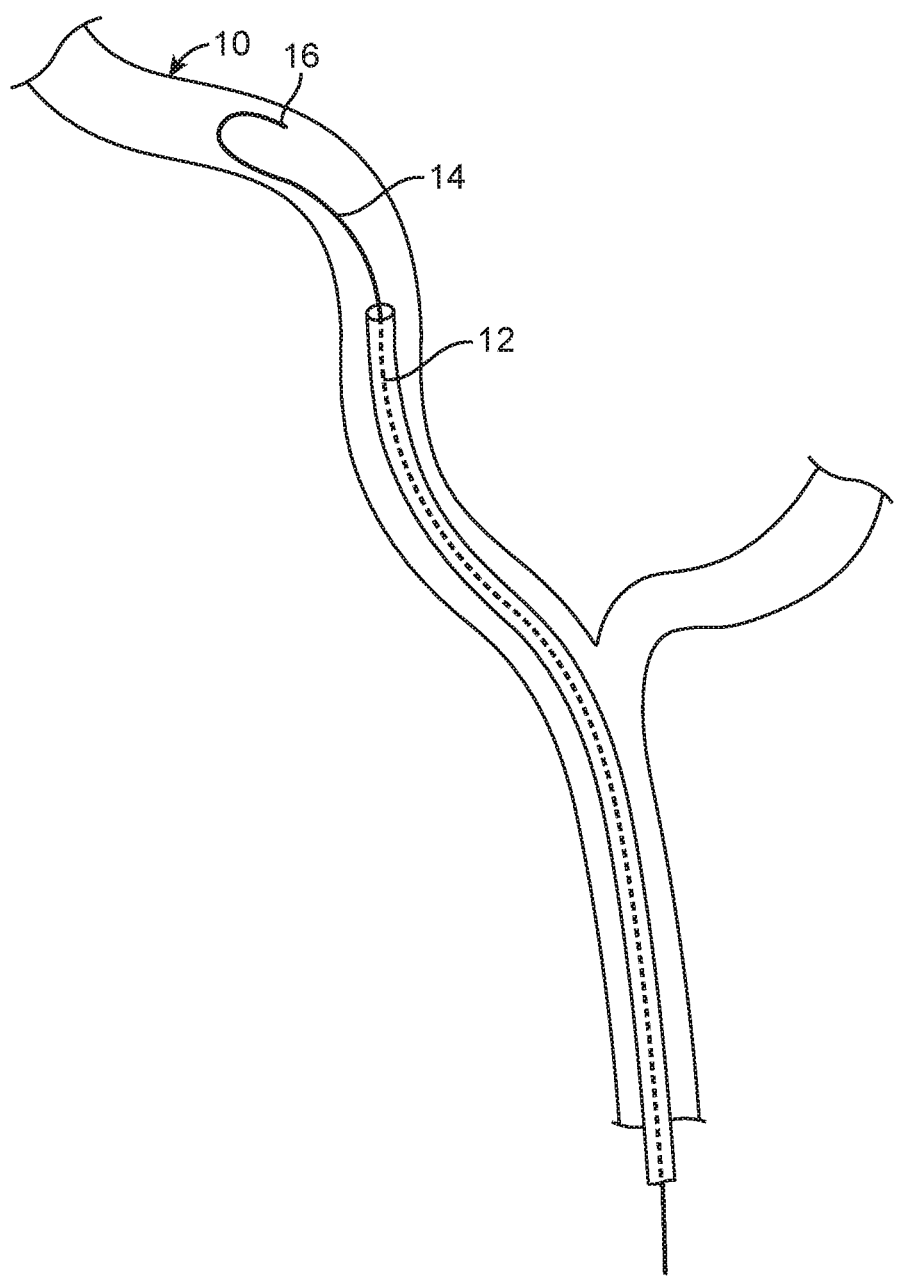
FIG. 1 illustrates a traditional J-tip guidewire being used with a catheter.

The ideas presented in this disclosure can be used in any corporeal lumen or tubular organ/duct within the body, but as described above can reduce undesired complications when used within the vasculature, especially delicate vasculature such as the cerebral vasculature. However, unless specifically noted, variations of the device and method are not limited to use in the cerebral vasculature. Instead, the invention may have applicability in various any part of the body. Moreover, the invention may be used in various procedures where the benefits of the method and/or device are desired.

FIG. 2A illustrates an example of an improved guidewire 100 having a guidewire body 102 and compliant member 104. The guidewire body 102 can be constructed according to any number of conventional methods. Typically, the guidewire body 102 comprises a solid core member that allows for tracking and advancement of the guidewire through tortuous anatomy. In certain variations, the guidewire body 102 can include a lumen. The improved guidewire 100 also includes an expandable tip structure or compliant structure 104. The compliant structure 104 is fabricated to be collapsible when positioned within a catheter that would apply a constraining force on the fully expanded profile of the compliant structure 104. Upon removal of the constraining force, or when advanced from the distal end of the catheter, the compliant structure 104 assumes an expanded profile as shown. The expanded profile is greater than a cross sectional measurement or radial dimension of the distal end of the guide wire body 102. Sizing of the compliant structure 102 in this manner allows the compliant structure 104 to serve as a temporary anchor when placed within a lumen having a smaller or the same diameter as that of the compliant structure 104.

The compliant structure 104 can function as a soft tip that causes significantly less trauma than a regular guidewire tip or the J-tip. The compliant tip or structure 104 expands radially away from an axis of the guidewire body. This radial expansion increases the contact surface between the compliant structure 104 and the lumen wall to better distribute any forces applied by the guidewire to the lumen wall as compared to the traditional guidewire or J-tip.

Variations of the device can include a compliant structure 104 with an expanded diameter as small as that of a standard guidewire tip, e.g. in the range of 0.010" to 0.016". Alternate variations can include a compliant structure 104 expanded diameter that is anywhere from approximately 1 mm to 4 mm, but could range from 0.5 mm up to 6 mm.

As noted above, the compliant tip structure 104 is collapsible for entry into and deliverability through the microcatheter, and then can self-expand once unconstrained by the microcatheter or other constraining member.

The shape of the compliant structure 104 can comprise any shape that permits anchoring within a vessel. In some examples, the shape of the compliant structure 104 is a spherical or ball shape. Alternatively, the shape can comprise an elongated shape, an egg shape, football shaped, elliptical, conical, cylindrical, or similar type of structure.

FIG. 2B illustrates a magnified view of a distal section of a guidewire 100. As shown the guidewire comprises a compliant structure 104 at the distal portion of a guidewire body where a portion of the elements forming the compliant structure continuously extend along a section 106 of the guidewire body. This integral extension of the compliant structure can minimize or eliminate the number of joints or connections at the distal end of the guidewire. The presence of joints between the guidewire body and compliant structure can impede the ability of the device to assume a sufficiently reduced profile or can interfere with the geometry/stiffness of the device causing problems when navigating the device through tortuous anatomy. Furthermore, joints can lead to potential failure locations, and may lead to fractured and loss of components within the body. Such joints may include welded, glued, or otherwise separately joined pieces into one or more points of connection.

Figure 3A:
FIG. 3A illustrates a plurality of elements or struts that can form compliant structure.
Figure 3B:
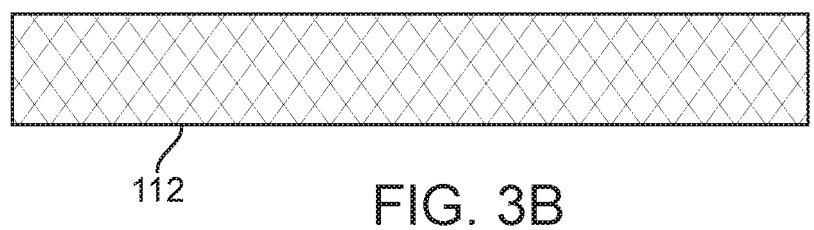
FIG. 3B represents an alternative of a compliant structure formed as a discrete or separate structure, such as a discrete braid or laser cut tube or sheet.
Figure 3C:
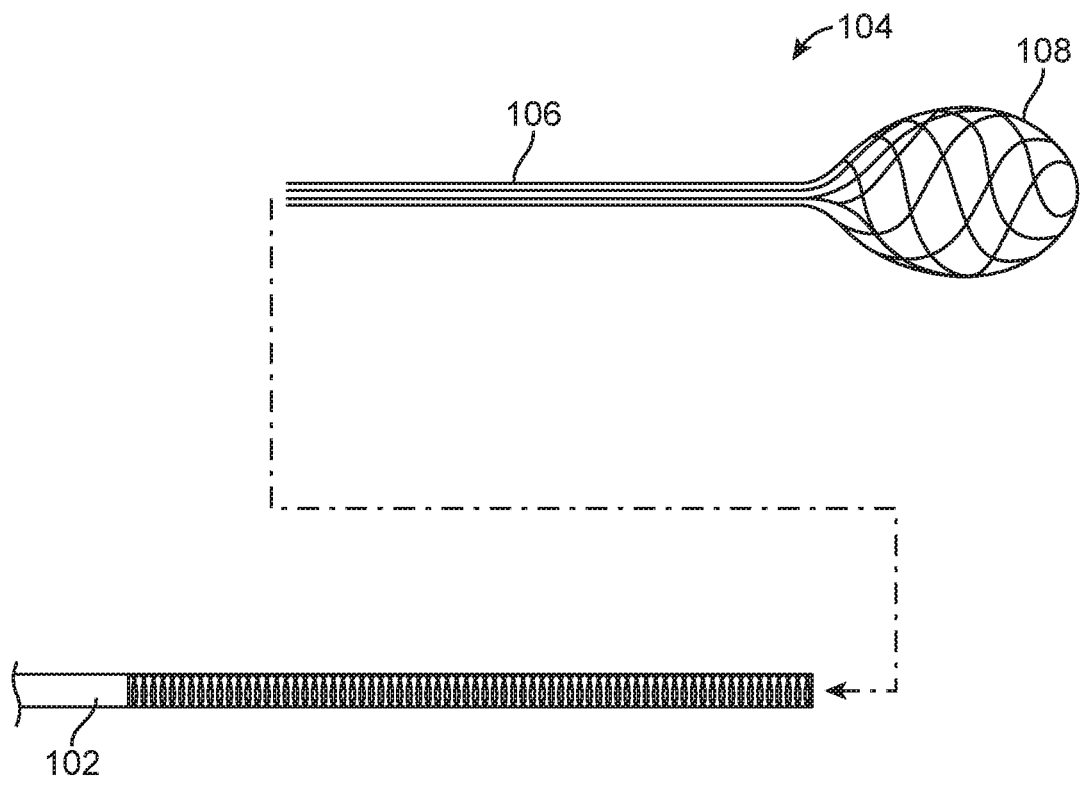
FIG. 3C illustrates an expandable tip structure or compliant structure having a continuous or integral proximal section, shown apart from its location of attachment to a guidewire body.

FIGS. 3A and 3C illustrate a plurality of elements or struts 110 that can form the compliant structure. As shown, the elements or struts 110 are continuous such that a distal portion can be fabricated to form the expandable or anchoring portion 108 of the compliant structure 104. The proximal section 106 of the compliant structure 104 remains continuous (and therefore integrally formed with the anchoring portion 108) and can be affixed to the guidewire body 102 such that the proximal section 106 of the compliant structure 104 extends along a portion of the guide wire body 102. The proximal section 106 can comprise a proximal extension of the elements 110 that conforms closely to the guidewire body 102 and does not expand away from the body 102. In the area of the proximal section 106, the guidewire body 102 can be of a somewhat smaller diameter so that the combination of the body 102 and the elements 110 of the proximal section 106 is substantially similar in overall diameter to the portion of the body 102 that is adjacent to and proximal of the proximal section 106. The elements 110 in the proximal section 106 can extend longitudinally and generally parallel to each other and to the guidewire body 102, or they can be braided together to form a tube that closely surrounds the body 102, or coiled or wound closely around the body 102. In certain variations, elements or struts 110 run continuously to the center of the guide wire 102 construction from the anchoring portion 108 and then back again to the center of the guide wire 102 as illustrated in FIG. 3C.

In one variation, the elements or struts 110 comprise superelastic nitinol wire, with several wires woven or braided together and heat set to form the anchoring portion 108 as shown in FIG. 3C. In some variations, the anchoring portion 108 can be heat set. The diameter of the elements can vary depending upon the desired properties of the compliant structure 104. In one example, the elements or struts 110 can comprise 0.001" to 0.003" diameter wire. The elements can be formed from a variety of materials, including but not limited to solid Nitinol wire, a shape memory alloy, a metal alloy or a hypotube filled with a platinum core (e.g., a drawn filled tube). In certain variations the drawn filled tube (DFT) wire comprises platinum and Nitinol, e.g. 30% platinum and 70% Nitinol. Decreasing the amount of platinum and increasing the Nitinol increases the wire strength and results in higher column strength. In yet another example, the elements 110, can be processed to produce the desired properties.

Additionally, the compliant structure can be formed with a mixture of wires of different materials, such as Nitinol and platinum wires, or wires of different size or cross-sectional geometry (i.e. flat wire, square wire, or ribbon wire, etc.)

The remaining construction of attaching the compliant structure to the guidewire assembly is readily apparent to anyone skilled in the art. In one variation, the proximal end of the elements 110 could be covered with a standard stainless coil or similar structure. Alternatively, or in combination the proximal end of the elements 110 could be bonded (such as adhesive bonded) to a ground core wire. The joined assembly could be covered with PTFE (common in the industry) or with a hydrophilic coating (also common in the industry). It could also be left uncoated if desired.

In alternative variations, the compliant structure 104 can be formed as a separate or discrete structure, such as a separate or discrete braid or laser cut tube or sheet (see FIG. 3B), and attached to the distal end of the guidewire body 102. The attachment method could consist of welding, soldering, crimping, adhesive bonding, etc. However, in such a case, the guidewire body can be configured to transition between the guidewire body and the compliant structure. Such a transition will prevent a sharp bend from forming between the guidewire body 102 and the anchor portion 108 (or the compliant portion 104).

Figure 4A:
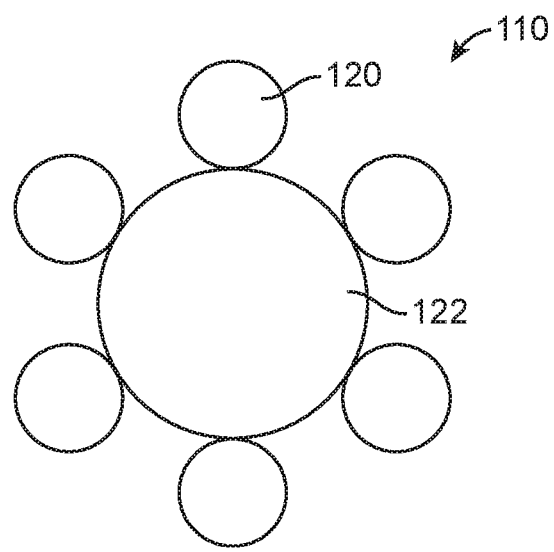
FIGS. 4A and 4B show cross sectional view of an example of a variation of an element or strut comprising a plurality of wires or a DFT material.
Figure 4B:
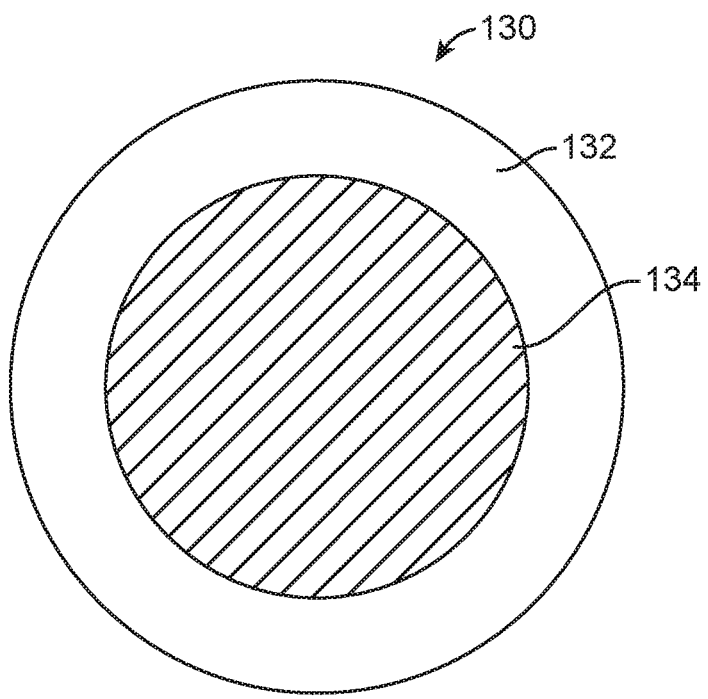

FIGS. 4A and 4B show cross sectional view of an example of a variation of an element or strut 110 (for use in the compliant structure 104) comprising a wire. As shown, the wire can take any of a number of configurations depending on the particular application. For example, individual wires (forming the elements or struts) can themselves comprise a bundle of smaller wires or filaments. In addition, the wires can be selected from materials such as stainless steel, titanium, platinum, gold, iridium, tantalum, Nitinol, alloys, and/or polymeric strands. In addition, the wires used in constructing the compliant structure 104 may form a heterogeneous structure having combinations of wires of different materials to produce a guidewire or compliant structure having the particular desired properties. For example, one or more wires of the compliant structure 104 or the body 102 may comprise a shape memory or superelastic alloy to impart predetermined shapes or resiliency to the device. In some variations, the mechanical properties of select wires can be altered. In such a case, the select wires can be treated to alter properties including: brittleness, ductility, elasticity, hardness, malleability, plasticity, strength, and toughness.

The compliant structure 104 or the guidewire body 102 may include a number of radiopaque wires, such as gold or platinum wires for improved visibility under fluoroscopic imaging. In other words, any combination of materials may be incorporated into the device. In addition to the material choice, the size of the wires may vary as needed. For example, the diameters of the wires may be uniform or may vary as needed.

In addition, the individual wires may have cross-sectional shapes ranging from circular, oval, D-shaped, rectangular, etc. FIG. 4A illustrates one possible variation in which a number of smaller-diameter wires 120 are positioned around a central larger-diameter wire 122. Moreover, the compliant structure 104 is not limited to having wires having a uniform cross-sectional shape or size. Instead, the device can have wires having non-uniform cross-sectional shapes. For example, any one or more of the wires 120, 122 can have a different cross-sectional shape or size than a remainder of the wires. Clearly, any number of variations is within the scope of this disclosure.

In another variation depicted in FIG. 4B, one or more of the struts or elements used in the compliant structure 104 or the body 102 can comprise a Drawn Filled Tube (DFT) such as those provided by Fort Wayne Metals, Fort Wayne, Ind. As shown in FIG. 4B, such a DFT wire 130 can comprise a first material or shell 132 over a core of a second material 134 having properties different from those of the shell. While a variety of materials can be used, one useful variation includes a DFT wire having a superelastic (e.g., Nitinol) shell with a radiopaque material core within the superelastic shell. For example, the radiopaque material can include any commercially used radiopaque material, including but not limited to platinum, iridium, gold, tantalum, or similar alloy. One benefit of making a compliant structure from DFT material is that rather than employing one or more discrete radiopaque wires or elements in the compliant structure, the entire compliant structure can be fabricated from a superelastic material while, at the same time, the superelastic compliant structure is radiopaque due to the core of radiopaque material within the superelastic shell. Any suitable composite DFT material can be employed in some or all of the elements 110 of the compliant structure 104.

As noted above, the construction of the compliant structure can include single wires or additional wires, having properties or joined (e.g. braided, woven or coiled) in a variety of patterns to obtain desired mechanical properties based on the intended application of the device. For example, in many variations, the wires, as shown in FIG. 3C can take a braided mesh shape, where the interlacing of the individual elements helps generate the desired radial force.

This radial force can be modified by altering the pattern of the elements or wires and/or increasing or decreasing the number or density of crossings that the wires make. The radial force can also be modified by altering the size of the wires, the specific alloy of wire used, and the processing methods. However, the anchor portion of the compliant structure, or the entire compliant structure can be configured to be axially compressible so as to absorb axial compression (e.g., the compliant structure readily compresses or behaves similar to a spring when an axial force of the sort typically encountered in the advancement of endovascular devices is applied at the distal tip). This feature allows the compliant structure to maximize the atraumatic interaction if it were to be inadvertently advanced into the vessel wall. As noted above, the portion of the guidewire adjacent to the anchor portion should also be configured to prevent sharp bends occurring between the anchor portion and guidewire body. In any case, the construction and orientation of the elements and/or struts forming the compliant structure can be chosen to obtain the desired properties of outward radial force (for anchoring and stability within the vessel) and axial compliance (for minimum traumatic interaction with the vessel wall).

Figure 5A:
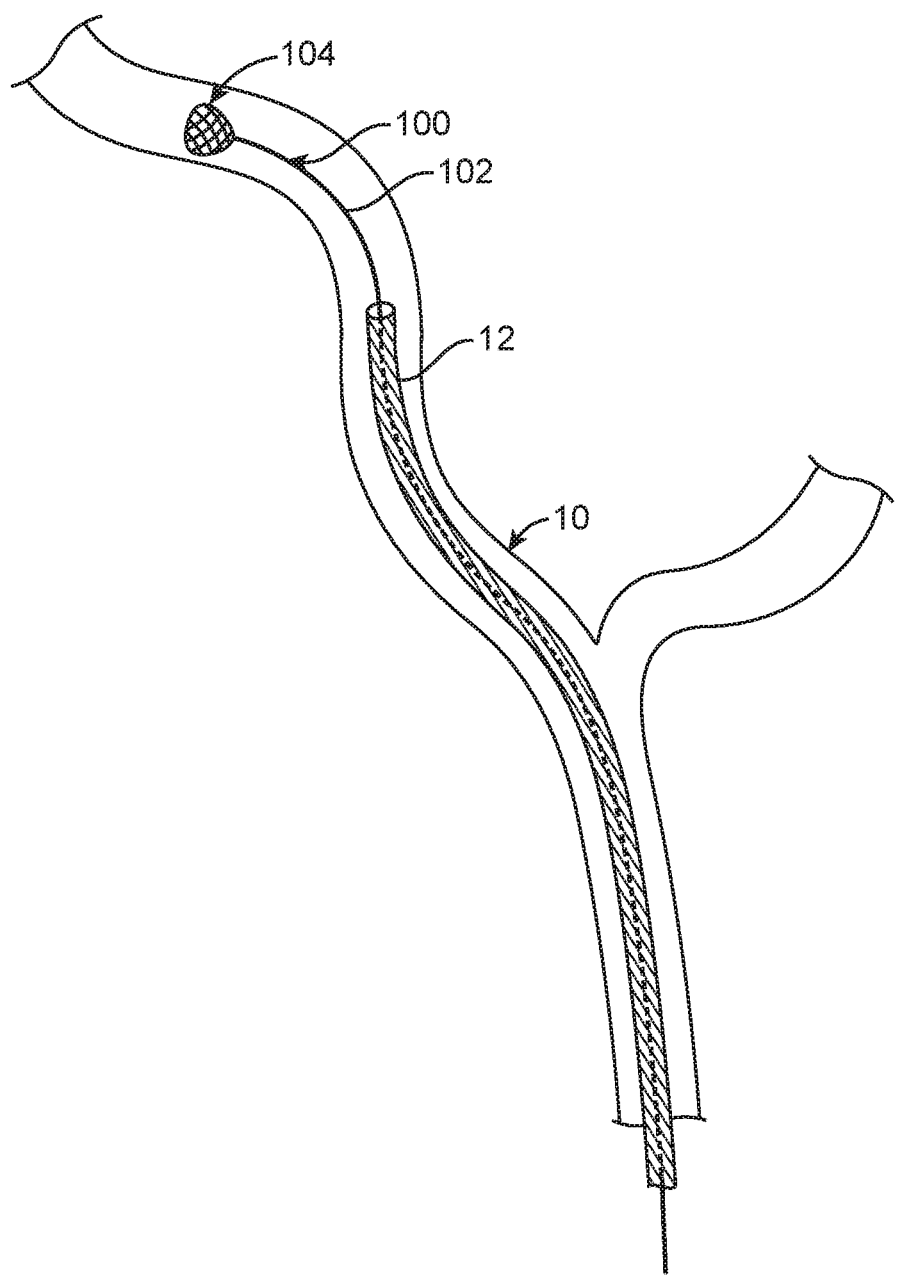
FIG. 5A illustrates one example of a guidewire deployed through a microcatheter where the anchoring portion of the compliant member provides an atraumatic tip to the guidewire.

FIG. 5A illustrates one example of method of using a guidewire 100 deployed through a microcatheter 12 where the anchoring portion of the compliant member 104 provides an atraumatic tip to the guidewire 100. As illustrated, the compliant member 104 comprises a plurality of elements in that can move relative to each other causing the frame member to be compliant while provide a uniform radial force in an outward circumferential direction from the guidewire body. This radial force reduces trauma to the vessel regardless of the direction in which the compliant member 104 engages the vessel 10. Therefore, the catheter 12 can be withdrawn or re-inserted over the guidewire 100 (or inserted over the guidewire 100 if the guidewire 100 is present before catheter insertion), and optionally a second catheter or other over-the-wire device can be inserted over the guidewire 100 with a minimum of trauma to the vessel wall.

In the variation shown in FIG. 5A, the compliant member 104 is sized such that the anchoring portion does not engage the wall of the vessel but simply serves to prevent the end of the guidewire 100 from causing trauma as the catheter 12 is removed and exchanged with a second catheter (not illustrated).

Figure 5B:
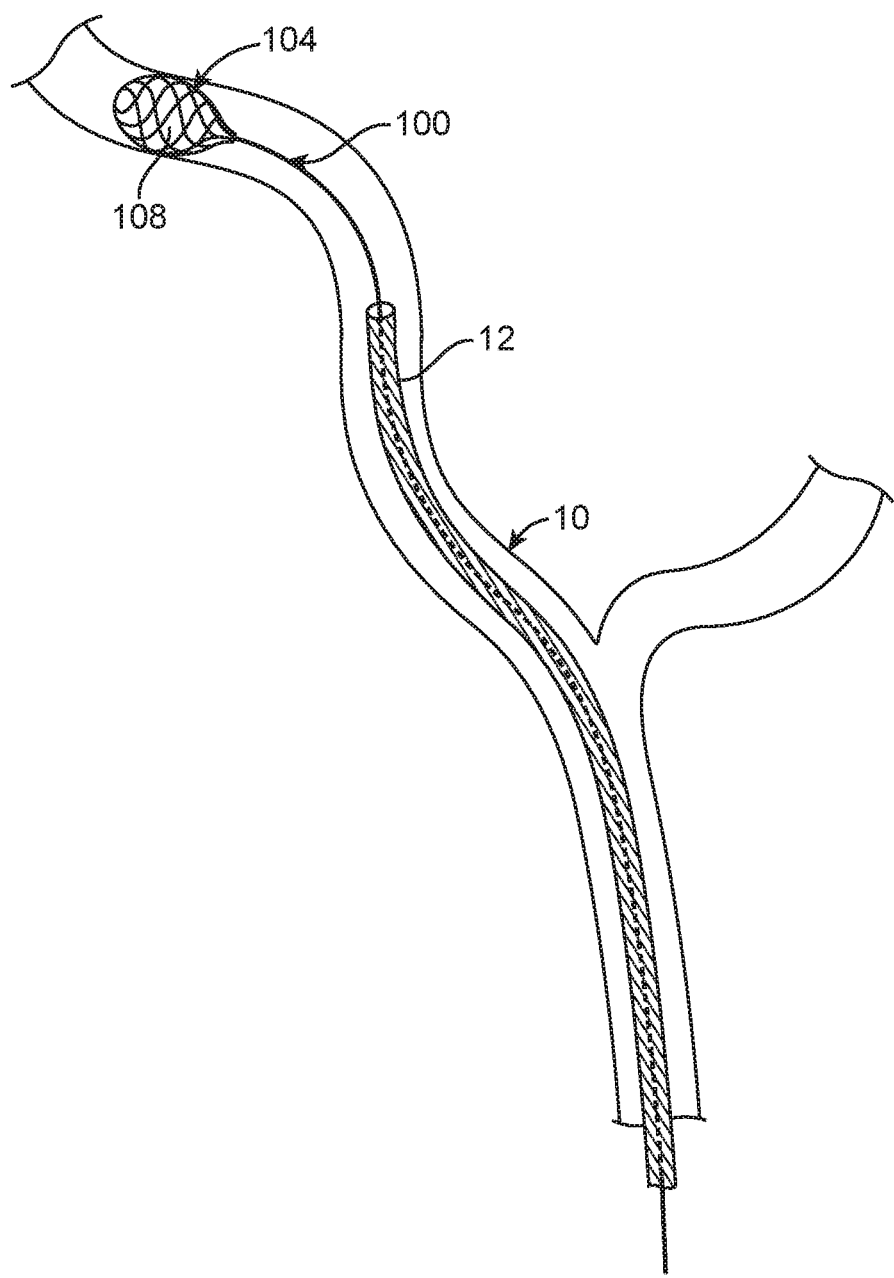
FIG. 5B illustrates one example of a guidewire deployed through a microcatheter where the anchoring portion of the compliant member provides an atraumatic tip to the guidewire.

FIG. 5B illustrates another example of a method of using a guidewire 100 where an anchoring portion 108 is sized to have a larger profile than the intended vessel. For example, a physician can select an anchoring portion with an expanded profile of 3 mm OD and place the guidewire into a vessel of a smaller diameter (e.g., 2.5 mm). The configuration of the struts or elements in the anchoring portion 108 exerts a radial force against the vessel wall. As noted above, the radial force can be applied uniformly about a perimeter of the anchoring portion 108. The application of force about the circumference of the vessel distributes force to lessen trauma as well as anchor the guidewire to facilitate improved catheter exchange. The relative sizing of the anchoring portion 108 to the vessel immobilizes the tip of the guidewire 108 during removal of the catheter 12 and further reduces the ability of the tip to engage in undesired motion during the exchange where a second catheter is advanced over the guidewire 100, which remains in place. Therefore, the catheter 12 can be withdrawn or re-inserted over the guidewire 100 (or inserted over the guidewire 100 if the guidewire 100 is present before catheter insertion), and optionally a second catheter or other over-the-wire device can be inserted over the guidewire I 00 with a minimum of trauma to the vessel wall.

The anchoring effect of the anchoring portion can serve to not only minimize undesired motion of the guidewire tip, but it may also facilitate the advancement of a second catheter (e.g. a second microcatheter) or other device, especially if the second catheter (or similar device) is relatively large or bulky. The anchoring of the tip of the wire gives more stability for the entire guidewire assembly, which then provides more support for the navigation of the new microcatheter.

It should be noted that the amount of "anchoring" that the compliant member delivers can be adjusted by varying the construction of the compliant member. For example, the OD of the anchoring portion, the OD of the struts, elements, and/or wires used in fabricating the device, the number of wires used, the pattern/density of the wires creating the structure, the number of crossings, and to a lesser extent, variations in the nitinol alloy and processing parameters can all be adjusted to provide a guidewire device for use in specific parts of the anatomy.

Figure 6A:
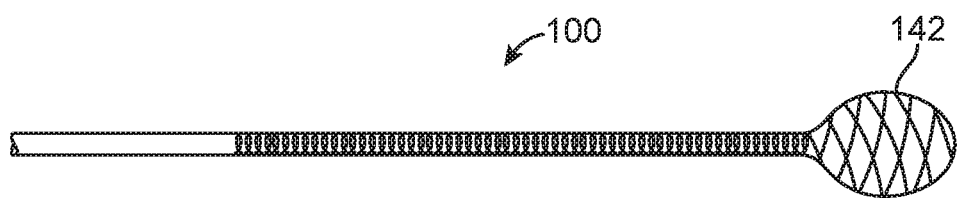
FIGS. 6A to 6E illustrate a number of profiles and shapes for the anchor portion of the compliant structure.
Figure 6B:
Figure 6C:
Figure 6D:
Figure 6E:

The diameter or expanded profile size of various anchoring portions can range from 1 mm to 4 mm, and/or otherwise as stated above. However, variations of the device can include sizes outside of this stated range. In addition, the length of the anchoring portion can range from between 2 mm up to 10 mm or even longer. Furthermore the shape of the anchoring portion in the expanded configuration can vary. As shown above and in FIG. 6A, the anchoring portion can comprise a spherical profile 142. In such a case, the diameter of the anchoring portion is generally uniform. FIG. 6B illustrates an elliptical, or football shaped profile 144 where the maximum diameter is located towards a center of the anchoring portion (as measured along an axis of the guide body of the guidewire. FIG. 6C illustrates a variation of an egg-shaped 145 anchoring portion where the maximum diameter is offset towards either a proximal or distal end of the anchoring portion. FIG. 6D illustrates a conical or near conical 146 profile. FIG. 6E illustrates a cylindrical profile 148, where the cylindrical profile 148 can include either an open or closed face at a distal end of the anchoring portion.

It should also be noted that although this disclosure is aimed at an exchange length guidewire, this atraumatic tip structure could be manufactured in a shorter (i.e. standard) guide wire length. In this case, the physician would remove the original procedural guidewire and replace it with any of the variants of the expandable-tipped or ball-tipped guidewire disclosed here. This could be desired if the physician does not plan to replace or exchange a microcatheter but nonetheless prefers a wire that is more atraumatic and/or offers anchoring for enhanced navigation or manipulation of the catheter.

A number of embodiments of the invention have been described. Nevertheless, it will be understood that various modifications may be made without departing from the spirit and scope of the invention. Combination of the aspects of the variations discussed above as well combinations of the variations themselves are intended to be within the scope of this disclosure.

Various changes may be made to the invention described and equivalents (whether recited herein or not included for the sake of some brevity) may be substituted without departing from the true spirit and scope of the invention. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present. More specifically, as used herein and in the appended claims, the singular forms "a," "and," "said," and "the" include plural references unless the context clearly dictates otherwise.

What is claimed is:

1. A guidewire for advancing through a body lumen in a tortuous anatomy, the guidewire comprising:
   a guidewire body extending between a proximal portion and a distal portion, the guidewire body comprising an elongated shape and configured to navigate the tortuous anatomy;
   a plurality of elements arranged to form a frame member having a diameter greater than a cross sectional diameter of the distal portion of the guidewire body;
   where the plurality of elements in the frame member can move relative to each other causing the frame member to be compliant and provide a radial force in an outward circumferential direction from the guidewire body when released from a constraining force; and
   the plurality of elements converging from a proximal region of the frame member to extend proximally from the frame member along the distal portion of the guidewire body, thereby forming a proximal extension of the plurality of elements, where the plurality of elements are continuous from the frame member into the proximal extension along the distal portion of the guidewire body.

2. The guidewire of claim 1, wherein the guidewire body comprises a core member and where the plurality of elements are affixed to the core member along the proximal extension of the plurality of elements.

3. The guidewire of claim 2, wherein the plurality of elements, in the proximal extension, are not radially expandable away from the core member.

4. The guidewire of claim 1, wherein the frame member comprises a shape selected from the group consisting of spherical, egg-shaped, football-shaped, elliptical, conical, cylindrical.

5. The guidewire of claim 1, wherein the plurality of elements comprises at least a first strut and a second strut, and wherein a cross sectional area of the first strut is different than a cross sectional area of the second strut.

6. The guidewire of claim 1, wherein the plurality of elements forming the frame member are interwoven to form the frame member.

7. The guidewire of claim 1, wherein the plurality of elements forming the frame member are braided to form the frame member.

8. The guidewire of claim 1, wherein the frame member is permeable to allow fluid flow therethrough.

9. The guidewire of claim 1, where at least one of the plurality of elements forming the frame member comprises a material selected from the group consisting of a drawn filled tube, a nitinol wire, a shape memory alloy, a superelastic alloy, a stainless steel material, and a platinum material.

10. The guidewire of claim 1, wherein the plurality of elements, in the proximal extension, are bonded to the guidewire body.

11. The guidewire of claim 1, wherein the plurality of elements in the proximal extension increase a column strength of distal portion of the guidewire body.

12. The guidewire of claim 1, wherein the guidewire body comprises a core member and wherein the plurality of elements, in the proximal extension, are affixed against the core member along the distal portion of the guidewire body.

13. A guidewire for advancing through a body lumen in a tortuous anatomy, the guidewire comprising:
- an elongated member extending between a proximal portion and a distal portion, the elongated member configured to navigate the tortuous anatomy; and
- a distal structure disposed at the distal portion of the guidewire body, the distal structure having: (a) a proximal region extending along the distal portion of the elongated member, and (b) an expandable member extending distally from the proximal region and configured to expand into contact with a wall of the body lumen,
- wherein the distal structure is formed of a plurality of woven filaments, each of the filaments extending between corresponding first and second ends, wherein the first and second ends of each of the respective filaments are located at the proximal region of the distal structure.

14. The guidewire of claim 13, wherein the elongated member comprises a solid core member.

15. The guidewire of claim 13, wherein the elongated member includes a lumen.

16. The guidewire of claim 13, wherein one or more of the filaments comprise a wire formed of a first material over a core of a second material, the second material being radiopaque.

17. The guidewire of claim 13, wherein the distal structure further includes a coating.

18. The guidewire of claim 13, wherein the elongated member includes a coil, and wherein at least a portion of the proximal region of the distal structure is surrounded by the coil.

19. The guidewire of claim 13, wherein the plurality of filaments diverge from the distal portion of the elongated member to form the distal structure.

20. The guidewire of claim 13, wherein the first and second ends of each of the plurality of filaments is affixed to a core wire.

* * * * *

UNITED STATES PATENT AND TRADEMARK OFFICE
CERTIFICATE OF CORRECTION

PATENT NO. : 11,497,895 B2
APPLICATION NO. : 16/561526
DATED : November 15, 2022
INVENTOR(S) : Martin et al.

It is certified that error appears in the above-identified patent and that said Letters Patent is hereby corrected as shown below:

In the Claims

In Column 12, in Claim 9, Line 56, delete "where" and insert -- wherein --, therefor.

In Column 12, in Claim 11, Line 67, delete "of distal" and insert -- of the distal --, therefor.

Signed and Sealed this
Twentieth Day of December, 2022

Katherine Kelly Vidal
*Director of the United States Patent and Trademark Office*